United States Patent [19]

Weber et al.

[11] Patent Number: 4,906,779

[45] Date of Patent: Mar. 6, 1990

[54] N,N'-DISUBSTITUTED GUANIDINES AND THEIR USE AS EXCITATORY AMINO ACID ANTAGONISTS

[75] Inventors: Eckard Weber, Portland; John F. Keana, Eugene, both of Oreg.

[73] Assignee: State of Oregon, acting by and through the Oregon State Board of Higher Education, acting for and on behalf of the Oregon Health Sciences University, Portland, Oreg.

[21] Appl. No.: 237,367

[22] Filed: Aug. 29, 1988

Related U.S. Application Data

[63] Continuation-in-part of Ser. No. 1,545, Jun. 26, 1987, which is a continuation-in-part of Ser. No. 884,150, Jul. 10, 1986.

[51] Int. Cl.$^4$ ............................................. C07C 129/12
[52] U.S. Cl. .................................................... 564/238
[58] Field of Search .......................... 564/238; 514/482

[56] References Cited

PUBLICATIONS

Drenka, I. V. et al Zh. Neorg. Khim 26(3) 643–9, 1981.

*Primary Examiner*—Paul J. Killos
*Attorney, Agent, or Firm*—Millen, White & Zelano

[57] ABSTRACT

Disubstituted guanidines, e.g., N,N'-di-m-tolyl guanidine, N,N'-di-o-ethylphenyl guanidine, N,N'-di-m-ethylphenyl guanidine, and N,N'-di-o-iodophenyl-guanidine, exhibit a high binding affinity to phenylcyclidine (PCP) receptors. These guanidine derivatives act as non-competitive blockers to glutamate induced responses of the NMDA receptor by acting as blockers for the ion channel of the NMDA receptor-ion channel complex. These compounds thus exert a neuroprotective property and are useful in the therapeutic treatment of neuronal loss in ischemia, hypoxia, hypoglycemia, and brain and spinal cord trauma as well as being useful for the treatment of epilepsy, Alzheimer's disease, Amyotrophic Lateral Sclerosis, Huntington's disease, Down's Syndrome and other neurodegenerative disorders.

33 Claims, 1 Drawing Sheet

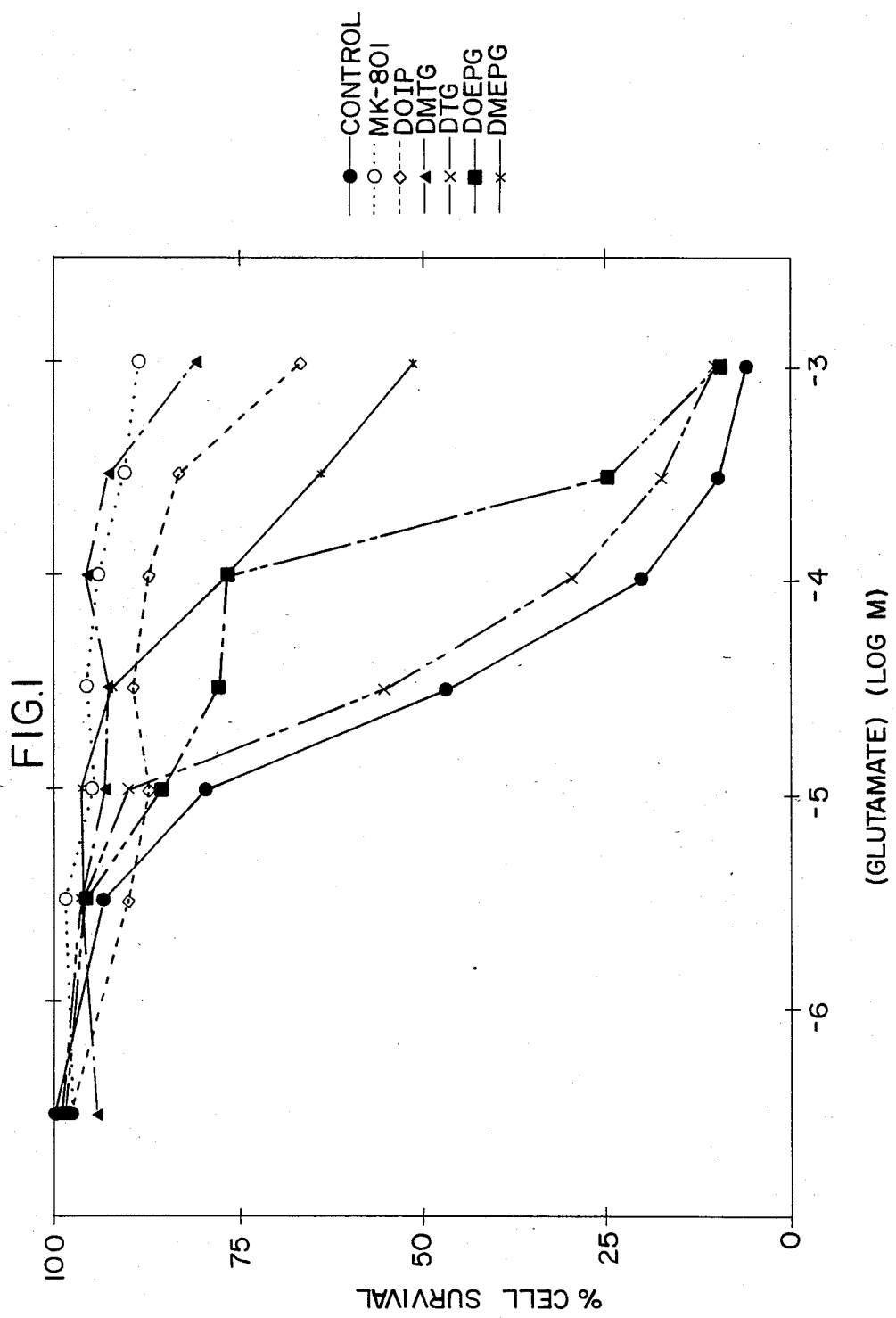

N,N'-DISUBSTITUTED GUANIDINES AND THEIR USE AS EXCITATORY AMINO ACID ANTAGONISTS

CROSS-REFERENCE TO RELATED APPLICATIONS

This application is a continuation-in-part of PCT/US87/01545 filed June 26, 1987 (and its U.S. counterpart), which is a continuation-in-part of U.S. Ser. No. 06/884,150 filed July 10, 1986.

BACKGROUND OF THE INVENTION

This invention relates to N,N'-disubstituted guanidine analogues, and to compounds and pharmaceutical compositions comprising the same, which possess neuroprotective capability. This invention further relates to methods for treating any disease of the nervous system in which the pathophysiology of the disease involves excessive excitation of nerve cells by agonists of the N-methyl-d-aspartate (NMDA) receptor. Such excessive excitation can lead to dysfunction of the nervous system in the case of epilepsy and to nerve cell degeneration in cases of hypoxia, hypoglycemia, ischemia, trauma and in neurodegenerative diseases such as Huntington's chorea, Amyotrophic Lateral Sclerosis (ALS), Alzheimer's disease and Down's Syndrome.

A wide variety of substituted guanidines are disclosed in the patent literature. For example:

- U.S. Pat. Nos. 1,411,731 and 1,422,506 discloses diphenylguanidine as a rubber accelerator;
- U.S. Pat. No. 1,597,233 discloses N-o-tolyl-N'-phenyl-guanidine as a rubber accelerator;
- U.S. Pat. No. 1,672,431 discloses N,N'-di-o-methoxyphenylguanidine as being useful for therapeutic purposes, especially in the form of water-soluble salts;
- U.S. Pat. No. 1,730,338 discloses N-p-dimethylamino-phenyl-N' -phenylguanidine as a rubber accelerator;
- U.S. Pat. No. 1,795,738 discloses a process for the production of N,N'-dialkyl-di-substituted guanidines, including N-di-ethyl-N'-phenyl-guanidine, N-diethyl-N-isoamylguanidine, N-dimethyl-N'-isoamylguanidine and N-dimethyl-N'-ethylguanidine;
- U.S. Pat. No. 1,850,682 discloses a process for the preparation of disubstituted guanidine rubber accelerators bearing an additional substituent on the imine nitrogen atom;
- U.S. Pat. No. 2,145,214 discloses the use of disubstituted guanidines, e.g., diarylguanidines especially dixylylguanidine, as parasiticides;
- U.S. Pat. Nos. 2,254,009 discloses sym-di-2-octylguanidine and 2,274,476 and 2,289,542 disclose sym-dicyclohexylguanidine as insecticides and moth larvae repellents;
- U.S. Pat. No. 2,633,474 discloses 1,3-bis(o-ethylphenyl)guanidine and 1,3-bis(p-ethylphenyl)guanidine as rubber accelerators;
- U.S. Pat. No. 3,117,994 discloses N,N',N"-trisubstituted guanidines and their salts as bacteriostatic compounds;
- U.S. Pat. No. 3,140,231 discloses N-methyl- and N-ethyl-N'octylguanidines and their salts as antihypertensive agents;
- U.S. Pat. No. 3,248,246 describes (Example 5) a 1,3-disubstituted guanidine whose substituents are hydrophobic hydrocarbon groups, one of which is naphthylmethyl and the other is n-butyl;
- U.S. Pat. No. 3,252,816 discloses various N-substituted and unsubstituted cinnamyl-guanidines and generically the corresponding N'- and N"-alkyl substituted compounds and their salts as antihypertensive agents;
- U.S. Pat. No. 3,270,054 discloses N-2-adamant-1-yl- and N-2-homoadamant-1-yl-oxy-ethyl-thioethyl- and aminoethylguanidine derivatives bearing at most two lower alkyl groups on the N'- and/or N"-nitrogen atom as sympathicolytic and anti-viral agents;
- U.S. Pat. No. 3,301,755 discloses N-ethylenically unsubstituted- alkyl-guanidines and the corresponding N'- and/or N"-lower alkyl compounds as hypoglycemic and antihypertensive agents;
- U.S. Pat. No. 3,409,669 discloses N-cyclohexylamino-(3,3-dialkyl-substituted-propyl)-guanidines and the corresponding N'-alkyl- and/or N"-alkyl-substituted compounds as hypotensive agents;
- U.S. Pat. No. 3,547,951 discloses 1,3-dioxolan-4-yl-alkyl-substituted guanidines which have antihypertensive activity and discloses lower alkyl, including n-butyl, as a possible substituent on the other amino group;
- U.S. Pat. No. 3,639,477 discloses propoxylguanidine compounds as having anorectic properties;
- U.S. Pat. Nos. 3,681,459; 3,769,427; 3,803,324; 3,908,013; 3,976,787; and 4,014,934 disclose aromatic substituted guanidine derivatives wherein the phenyl ring can contain hydroxy and/or halogen substituents for use in vasoconstrictive therapy;
- U.S. Pat. No. 3,804,898 discloses N-benzycyclobutenyl and N-benzycyclobutenyl-alkyl-guanidines and the corresponding N-alkyl and/or N-alkyl-substituted compounds as hypotensive agents;
- U.S. Pat. No. 3,968,243 discloses N-aralkyl substituted guanidines and the corresponding N'-alkylnalkyl and N',N'-aralkyl compounds as being useful in the treatment of cardiac arrhythmias;
- U.S. Pat. No. 3,795,533 discloses o-halo-benzylideneaminoidines and their use as anti-depressants for overcoming psychic depression;
- U.S. Pat. No. 4,007,181 discloses various N,N'-disubstituted guanidines substitutes on the imine nitrogen atom by a adamantyl as possessing antiarrhythmic and diuretic activities;
- U.S. Pat. No. 4,051,256 discloses N-phenyl- and N-pyridyl-N'- cycloalkyl-guanidines as antiviral agents;
- U.S. Pat. Nos. 4,052,455 and 4,130,663 disclose styrylamidines, as analgesics agents or for the prevention of blood platelet aggregation;
- U.S. Pat. No. 4,109,014 discloses N-hydroxysubstituted guanidines and the corresponding N-methyl disubstituted guanidines as vasoconstrictor agents;
- U.S. Pat. No. 4,169,154 discloses the use of guanidines in the treatment of depression;
- U.S. Pat. No. 4,393,007 discloses N-substituted and unsubstituted, N-substituted methyl-N'-unsubstituted, monosubstituted and disubstituted-N-unsubstituted and substituted guanidines as ganglionic blocking agents; and U.S. Pat. No. 4,471,137 discloses N,N,N'N"-tetraalkyl guanidines as being sterically hindered bases useful in chemical synthesis.

U.S. Pat. No. 4,709,094 discloses 1,3-disubstituted-guanidines, e.g., 1-3-dibutyl-guanidine and 1,3 di-o-tolylquanidine, as sigma brain receptor ligands.

For examples of other substituted guanidines, see, e.g., U.S. Pat. Nos. 1,422,506; 1,642,180; 1,756,315; 3,159,676; 3,228,975; 3,248,426; 3,283,003; 3,320,229; 3,479,437; 3,547,951; 3,639,477; 3,784,643; 3,949,089; 3,975,533; 4,060,640 and 4,161,541.

Geluk, H. W., et al., *J. Med. Chem.*, 12,712 (1969) describe the synthesis of a variety of adamantyl disubstituted guanidines as possible antiviral agents, including N,N'-di-(adamantan-1-yl)-guanidine hydrochloride, N-(adamantan-1-yl-N'-cyclohexyl-guanidine hydrochloride and N-(adamantan-1-yl)-N'-benzyl-guanidine hydrochloride.

We have found that certain N,N"-disubstituted guanidines possess high PCP receptor binding activity.

The amino acid L-glutamate is widely thought to act as a chemical transmitter substance at excitatory synapses within the central nervous system. Neuronal responses to glutamate are complex and appear to be mediated by at least three different receptor types, i.e., KA, QA and NMDA subtypes, each being named for their relatively specific ligands, i.e., kainic acid, quisqualic acid and N-methyl-D-aspartic acid, respectively. An amino acid which activates one or more of these receptor types is referred to as an excitatory amino acid (EAA).

The NMDA subtype of excitatory amino acid receptors is activated during normal excitatory synaptic transmission in the brain. Activation of NMDA receptors under normal conditions is responsible for the phenomena of long-term potentiation, a memory-like phenomenon, at excitatory synapses. Excessive excitation of neurons occurs in epileptic seizures and it has been shown that over-activation of NMDA receptors contributes to the pathophysiology of epilepsy.

NMDA receptors are also strongly involved in nerve cell death which occurs following brain ischemia. Upon the occurrence of ischemic brain insults such as stroke or heart attack, an excessive release of endogenous glutamate occurs, resulting in the over-stimulation of NMDA receptors. Associated with the NMDA receptors is an ion channel. The recognition site, i.e., the NMDA receptor, is external to the ion channel. When glutamate interacts with the NMDA receptor, it causes the ion channel to open, thereby permitting a flow of cations across the cell membrane, e.g., $Ca^{2+}$ and $Na^+$ into the cell and $K^+$ out of the cell. It is believed that this flux of ions, especially the influx of $Ca^{2+}$ ions, caused by the interaction of glutamate with the NMDA receptor plays an important role in neuronal death. See, e.g., Rothman, S. M. and Olney, J. W., *Trends in Neurosci.* 10(7), 299–302 (1987).

Agents which block responses to NMDA receptor activation therefore have therapeutic uses in the treatment of neurological disorders such as epilepsy and also in the prevention of nerve cell death resulting from hypoxia or hypoglycemia or following brain ischemia which occurs during stroke, trauma and heart attack. A number of disorders of the nervous system are associated with neurodegeneration that may be caused by over-activation of NMDA receptors. Antagonists of NMDA receptor-mediated responses have potential therefore for the treatment of such disorders as Alzheimer's disease, Huntington's chorea, Amyotrophic Lateral Sclerosis and Down's Syndrome Research on the NMDA receptor-ion channel complex has led to the determination of a receptor site within the ion channel known as the PCP receptor. See Vincent, J. P., Kartalovski, B., Geneste, P., Kamenka, J. M. and Lazdunski, M., *Proc. Natl. Acad. Sci. USA* 76, 4678–4682 (1979); Zukin, S. R. and Zukin, R. S., *Proc. Natl. Acad. Sci. USA* 76, 5372–5376 (1979); Sonders, M. S., Keana, J. F. W. and Weber, E., *Trends in Neurosci.* 11(1), 37–40

1988); and Anis, N. A., Berry, S. C., Burton, N. R. and Lodge, D., *Br. J. Pharmacol.* 79, 565–575 (1983). Compounds which bind to the PCP receptor can act as an ion channel block, thereby interrupting the flow of ions through the cell membrane. In this manner, agents which interact with the PCP receptor act as non-competitive blockers reducing the agonist action of glutamate at the NMDA receptor.

Known PCP receptor ligands include PCP [angel dust], i.e., phencyclidine, analogues such as 1-[1-(2-thienyl)-cyclohexyl]-piperidine (TCP), benzomorphane (sigma) opiates, dioxylanes and 5-methyl-10,11-dihydro- 5H-dibenzo[A,D]cycloheptene-5,10-imine (i.e., the drug MK-801, see U.S. Pat. No. 4,399,141). See, also, Wong, E. H. F., Kemp, J. A., Priestly, T., Knight, A. R., Woodruff, G. N., and Iversen, L. I., *Proc. Natl. Acad. Sci. USA* 83, 7104–7108 (1986). MK-801 is apparently the most potent selective PCP receptor ligand/NMDA channel blocker known to date.

We have identified compounds which exhibit a high activity for binding to the PCP receptor and are structurally different from known PCP ligands.

SUMMARY OF THE INVENTION

It is an object of this invention to provide N,N'-disubstituted guanidines which exhibit a high affinity to the PCP receptor for the NMDA receptor-channel complex.

It is another object of the invention to provide N,N'-disubstituted guanidine to aid in PCP receptor research.

A further object of the invention is to provide N,N'-disubstituted guanidine useful for the treatment of neurological conditions such as epilepsy and those nervous system disorders associated with neurodegeneration.

It is a further object of the invention to provide a method for treating diseases of the nervous system associated with excessive excitation of nerve cells by agonists of the NMDA receptor.

It is yet a further object of the invention to treat dysfunction of the nervous system causing, for example, epilepsy, which is associated with excessive excitation of nerve cells by agonists of the NMDA receptor by the administration of effective amounts of N,N'-guanidine compounds having a high affinity for the PCP receptor.

It is yet a further object of the invention to treat neurodegenerative conditions and/or nerve cell death resulting from hypoxia, ischemia, hypoglycemia, brain and spinal cord trauma, and the like, by the administration of effective amounts of N,N'-disubstituted guanidine compounds having a high affinity for the PCP receptor.

It is yet a further object of the present invention to treat neurodegenerative conditions associated with the various neurodegenerative diseases such as Huntington's chorea, Amyotrophic Lateral Sclerosis, Alzheimer's disease and Down's Syndrome by the administration of effective amounts of N,N'-disubstituted quanidines having a high affinity for the PCP receptor.

Upon further study of the specification and appended claims, further objects and advantages of this invention will become apparent to those skilled in the art.

BRIEF DESCRIPTION OF THE DRAWING

Various other objects, features and attendant advantages of the present invention will be more fully appreciated as the same becomes better understood when considered in conjunction with the accompanying drawing wherein:

FIG. 1 is a graphical representation of the data resulting from the in vitro neurotoxicity assay described below. Cell survival was normalized as a percentage of highest cell count, with the results plotted against glutamate concentration.

DESCRIPTION OF THE PREFERRED EMBODIMENTS

The above-mentioned objects have been achieved by the determination of certain N,N'-disubstituted guanidines which exhibit a high binding affinity for the PCP receptor site.

The preferred N,N'-disubstituted guanidines of this invention are those of the formula

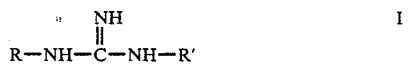

wherein R and R' each are an alkyl group of at least 4 carbon atoms or carbocyclic aryl groups of at least 6 carbon atoms, e.g., R and R', which can be the same or different, are alkyl of 4 or more carbon atoms, e.g., a 4 to 12 carbon atom, preferably a straight chain, alkyl group and more preferably a 4 to 8 carbon atom alkyl group, for example, butyl, isobutyl, tert-butyl, amyl, hexyl, octyl, nonyl and decyl; cycloalkyl of 3 to 12 carbon atoms, e.g., cyclopropyl, cyclopentyl, cyclohexyl, cycloheptyl, 1,4-methylene-cyclohexane, adamantyl, cyclopentylmethyl, cyclohexylmethyl, 1- or 2-cyclohexylethyl and 1-, 2- or 3-cyclohexylpropyl; carbocyclic aryl, alkaryl or aralkyl, e.g., of up to 18 carbon atoms and containing 1-3 separate or fused aromatic ings, e.g., phenyl, benzyl, 1- and 2-phenylethyl, 1-, 2-, or 3-phenylpropyl; o-, m-, or p-tolyl, m,m'-dimethylphenyl, o-, m-, or p-ethylphenyl, m,m'-diethylphenyl, m-methyl-m'-ethylphenyl and o-, m-, or p-propylphenyl, naphthyl, 2-naphthyl, and biphenyl, and heterocyclic aromatic rings including pyridyl, pyrazinyl, pyrimidyl, furyl, pyrrolyl, thienyl, thiazolyl, oxazolyl, imidazolyl, indolyl, and benzothiazolyl.

Additionally, 1, 2, 3 or more substituents may be present on the R and R'hydrocarbon groups, e.g., alkyl of 1-8 carbon atoms, e.g., methyl, ethyl; halo, e.g., chloro, bromo, iodo, fluoro; nitro; azido; cyano; isocyanate; amino; lower-alkylamino; di-loweralkylamino; trifluoromethyl; alkoxy of 1-8 carbon atoms, e.g., methoxy, ethoxy and propoxy; acyloxy, e.g., alkanoyloxy of 1-8 carbon atoms, e.g., acetoxy and benzoxy; amido, e.g., acetamido, N-ethylacetamido; carbamido, e.g., carbamyl, N-methylcarbamyl, N,N'dimethylcarbamyl; etc.

Especially preferred are compounds of Formula I wherein R and R' each are phenyl groups, which need not necessarily be identical, substituted with one or more of the foregoing substituents, for example, in the o-, m- or p-position or the o-, p- or m,m'-position, when the phenyl group is disubstituted, or R is as herein defined and R' is adamantyl.

Preferred compounds include N,N'-di-m-tolylguanidine (DMTG); N,N'-di-o-iodo-phenyl-guanidine (DOIPG); N,N'-di-o-ethylphenyl-guanidine (DOEPG); and N,N'-di-m-ethylphenyl-guanidine (DMEPG).

he above-listed compounds are disubstituted guanidines, which class of compounds are the subject of U.S. Pat. No. 4,709,094, whose disclosure is incorporated herein by reference, the preferred of which are described therein by the formula:

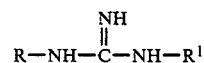

wherein R and R¹ are each independently alkyl, cycloalkyl, carbocyclic aryl, alkaryl or aralkyl. As a class, these compounds are described in this patent as exhibiting a highly selective binding activity to the sigma brain receptor. DTG itself also exhibits a strong selectivity for the sigma receptor (Weber, E., Sonders, M., Quarum, M., McLean, S., Pou, S., & Keana, J. F. W., Proc. Natl. Acad. Sci. USA 83, 8786–8788 (1986)). However, it has now been determined that certain specific members of this class of disubstituted guanidines additionally exhibit a high binding activity for the PCP receptor.

These N,N'-disubstituted guanidines can readily be prepared by conventional chemical reactions, e.g., when R and R' are the same, by reaction of the corresponding amine with cyanogen bromide. Other methods which can be employed include the reaction of an amine with a preformed alkyl or aryl cyanamide. See Safer, S. R., et al., J. Oro. Chem. 13:924 (1948). This is the method of choice for producing N,N'-disubstituted guanidines in which the substituents are not identical. For a recent synthesis of unsymmetrical guanidines, see G. J. Durant et al., J. Med. Chem. 28:1414 (1985), and C. A. Maryanoff et al., J. Org. Chem. 51:1882 (1986), incorporated by reference herein.

In a compositional aspect, this invention relates to a pharmaceutical composition in unit dosage form and adapted for systemic administration to a subject, e.g., a human being, comprising per unit dosage an amount of a N,N'-disubstituted guanidine effective to alter the brain NMDA receptor-mediated activity, wherein the N,N'-disubstituted guanidine has a high affinity for the PCP receptor.

In another compositional aspect, this invention relates to a neuroprotecting N,N'-disubstituted guanidine which exhibits a high binding activity with respect to the PCP receptor in mammalian nerve cells selected from the group consisting of N,N'-di-m-tolyl-guanidine; N,N'-di-o-iodo-phenyl-guanidine; N,N'-di-o-ethylphenyl-guanidine; and N,N'-di-m-ethylphenylguanidine and physiologically acceptable salts thereof.

In a method aspect, this invention relates to a method for treating or preventing neurodegenerative disorders, epilepsy or memory disorders comprising administering an effective amount of a N,N'-disubstituted guanidine having a high affinity for the PCP receptor to a subject in need of such treatment. Such N,N'-disubstituted guanidines possess utilities as non-competitive blockers of NMDA-receptor-mediated action.

In a further method aspect, this invention relates to a method of ameliorating the neurotoxic effect induced by glutamate interacting with the NMDA receptor of a nerve cell, comprising administering to a subject, e.g., a human being exhibiting symptoms of or susceptible to such neurotoxic effect a N,N'-disubstituted guanidine having a high affinity for the PCP receptor of the nerve cell in an amount effective to block the ion channel of the NMDA receptor-ion channel complex. The term "high affinity" means the compound exhibits an equilibrium dissociation constant of about 1 micromolar or less in a PCP receptor binding assay, typically a PCP receptor assay as described below.

In another method aspect, this invention relates to a method of inhibiting NMDA receptor-ion channel related neurotoxicity comprising administering to a mammal a N,N'-disubstituted guanidine possessing a high affinity for the PCP receptor of a nerve cell, in an amount effective to inhibit the neurotoxicity.

Such N,N'-disubstituted guanidines and other non-competitive blockers of NMDA receptor agonists can be determined by a method involving: (a) determining the binding affinity with respect to the PCP receptor by competitive displacement of tritiated TCP or MK-801; (b) evaluating the ability of compounds to block the passage of ions through ion channels by measurement of electrical current through the channel; (c) in vitro cytoxicity studies measuring the ability of the compound to prevent nerve cell death caused by exposure to glutamate; and (d) determination of in vivo neuroprotective ability using animal models.

Evaluation of the binding activity of organic compounds with respect to the PCP receptor is performed using radioligand binding assays. The compounds are tested to determine their ability to displace tritiatedTCP and tritiated-MK-801 which are used to label PCP receptors. Evaluating the competitive displacement binding data, the preferred compounds are those which exhibit a high affinity (i.e., low $IC_{50}$ value) for the PCP receptors.

Under the binding activity studies an $IC_{50}$ value of at most about 1000 nM, preferably at most about 500 nM, indicates a high binding affinity.

In the electrophysiological studies the compounds are evaluated with respect to their ability to block the ion channels of the NMDA receptor channel complex and thereby inhibit $Ca^{2+}$ and $Na^+$ ion flow into the nerve cell. Initially, the ion channels are opened by activating the NMDA receptor. Ion flow is determined by measuring the passage of electrical current and a decrease in electric current indicates blocking of the ion channel due to binding of a ligand at the PCP receptor site.

Blockage of the ion channel is a use-dependent activity. In other words, as more NMDA receptor-channel complexes are activated by glutamate, blockage of the channels by the non-competitive blocking agent become more effective.

In the neurotoxicity studies cultured mammalian neurons or cell lines expressing EAA receptors are exposed in vitro to glutamate and the compound under investigation. The survival percentage of cells indicates the ability of the compound to protect against glutamate-induced neuronal death. This vitro cell death assay is described in greater detail below.

In the in vivo neurotoxicity studies, the experimental model of McDonald, J. W., et al., (In: *Sigma and Phencylidine-like Compounds as Molecular Probes in Biology,* Ed. Domino, E. F., and Kamenka, J. M., pp. 697–707 (1988), NPP Books, Ann Arbor, Mich.) was employed. In this model, an NMDA injection into one cerebral hemisphere causes injury which resembles the lesion produced by hypoxia-ischemia. The ability of compounds to limit the NMDA-induced lesion is a measure of their neuroprotective properties; and, since the compounds are administered intraperitoneally, the model also provides information about a compound's ability to cross the blood-brain barrier.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire text of all applications, patents and publications, if any, cited above and below are hereby incorporated by reference.

EXAMPLES

In preparation Examples 1 and 2, melting points were determined in open capillary tubes on a Thomas-Hoover apparatus and are uncorrected. Analytical results for all compounds below were performed by Desert Analysis (Tucson, AZ) and were within +0.4% of theoretical values for the indicated elements. NMR spectra were recorded in $CD_3OD$ on a General Electric QE-300, and chemical shifts are reported in ppm relative to the residual signal of the deuterated solvent ($HCD_2OD$, 3.30). IR spectra were recorded on a Nicolet 5DXB FT-IR in KBr. All amines were purified by standard procedures, or where indicated were used directly as received. Cyanogen bromide was obtained from Aldrich Co., $CaH_2$ and stored over 4 A molecular sieves. $Et_2O$ was routinely distilled from benzophenone ketyl. All other solvents were reagent grade.

1. Preoaration of N,N'-di-o-iodophenyl-guanidine (DOIPG)

A solution of cyanogen bromide (4.40 g, 38.2 mmol) and 2-iodoaniline (4.14 g, 18.9 mmol) in $H_2O$ (70 ml) was heated at 70°–80° C. for 5 hours. The reaction mixture was decanted from an off-white solid (1.90 g) which was discarded, and the supernatant was heated at the same temperature an additional 16 hours. On cooling to 25° C., DOIPG precipitated from solution as its hydrobromide salt, was centrifuged off, and dried (500 mg, 10%). The thus formed white powder was dissolved in boiling $H_2O$ (20 ml), ad 5N NaOH (2 ml) was added to the clear solution. The resulting white precipitate (290 mg) was washed with $H_2O$ (3×4 ml), and crystallized from 95% EtOH, to give DOIPG (119 mg, 39% from the hydrobromide salt) as long white needles: mp 161°–162° C. One further crystallization provided the analytical sample: mp 161°–162° C.

Anal. Calcd for $C_{13}H_{11}N_3I_2$: C, 33.72; H, 2.39; N, 9.07.

Found: C, 33.80; H, 2.26: N, 8.78.

$^1H$ NMR: δ6.790 (t, J-7.8 Hz, 2H), 7.304 (t, J-7.8 Hz, 2H), 7.506 (d, J-7.8 Hz, 2H), 7.817 (d, J-7.8 Hz, 2H).

IR: 729, 753, 1456, 1502, 1572, 1613, 1647, 3056, 3387 $cm^{-1}$.

2. Preparation of N,N'-di-m-tolyl-guanidine (DMTG)

Cyanogen bromide (788 mg, 7.44 mmol) was placed in a 25 ml round bottom flask, and m-toluidine (1.89 g, 17.6 mmol) was added dropwise. After the exothermic reaction had subsided, the residue was taken up in $CH_2Clhd 2$ (20 ml), and was extracted with 5% HCl (5×10 ml). The aqueous extracts were adjusted to pH 10 with 6N NaOH. The resulting precipitate (674 mg, 38%) was filtered off and crystallized from EtOH/H$_2$O to give DMTG (240 mg, 14%) as white needles: mp 105°–106° C.

Anal. Calcd for C$_{15}$H$_{17}$N$_3$ C, 75.28; H, 7.16; N, 17.56. Found: C, 75.42; H, 7.11; N, 17.43.

$^1$H NMR: δ2.289 (s, 6 H), 6.814 (d, 2 H, J - 7.5 Hz), 6.939 (d, 2 H, J - 7.5 Hz), 6.981 (s, 2 H), 7.141 (t, 2 H, J - 7.5 Hz).

See also, Kazarinova et al., Zh. Anal. Khim; 28, p1853 (1973) and Chemical Abstracts 80:97021 (1973).

Other suitable N,N'-disubstituted guanidines can be prepared by similar procedures.

Experimental (Examples 3 and 4): Melting points were determined on a Thomas-Hoover melting point apparatus and are uncorrected. NMR spectra were recorded on a General Electric QE 300 spectrometer, and shifts are reported in ppm from the residual proton signal of the deuterated solvent (CHCl$_3$δ7.265). IR spectra were recorded on a Nicolet FDXB FTIR machine. All solvents and reagents were reagent grade, and were used as received. Microanalyses were performed by Desert Analytics of Tucson, AZ.

3. Preparation of N,N'-di-m-ethylphenyl-ouanidine (DMEPG)

A solution of cyanogen bromide (650 mg, 6.14 mmol) in Et$_2$O (1 ml) was added to 3-ethylaniline (1.42 g, 11.7 mmol). After the exothermic reaction had subsided, the viscous oil was heated under a stream of N$_2$ at 150° C. for 15 min, and then was allowed to cool to 25° C. The resulting solid was dissolved in 95% EtOH (20 ml), and 10% NaOH (20 ml) was added. A white precipitate formed and was filtered off, and recrystallized twice from 50% aqueous EtOH, to give N,N'-di-m-ethylphenyl-guanidine as white needles (620 mg, 20%): mp 96°–98° C., Anal. Calcd. for C$_{17}$H$_{21}$N$_3$: C, 76.37; H, 7.92; N, 15.72. Found: C, 75.93; H, 7.90; N, 15.76.

IH NMR (CDCl$_3$): δ1.216 (t, J=7.5 Hz, 6 H), 2.608 (q, J=7.5 Hz, 4 H), 6.937 (m, 6 H), 7.222 (t, J=7.8 Hz, 2 H).

IR (CDCl$_3$): 2971, 1629, 1589, 1490, 1417, 1217 cm$^{-1}$.

4. Preparation of N,N'-di-o-ethylphenyl-guanidine (DOEPG)

A solution of cyanogen bromide (1.41 g, 13.3 mmol) in 95% EtOH (3 ml) was added to an ice-cold solution of 2-ethylaniline (3.08 g, 25.4 mmol) in 95% EtOH (10 ml).

The reaction mixture was heated at 150° C. under a rapid stream of N$_2$ for 30 min, and was allowed to cool to 25° C. The resulting solid was dissolved in 95% EtOH (15 l), and 10% NaOH (30 ml) was added. White needles formed and were filtered off, and recrystallized twice from 25% aqueous EtOH, to give N,N'-di-o-ethylphenylguanidine as white needles (2.00 g, 59%): mp 158°–161° C. (lit.[1]: 161.5°–162° C.)

$^1$H NMR (CDCl$_3$): δ1.209 (t, J=7.5 Hz, 6 H), 2.653 (q, J=7.5 Hz, 4 H), 7.054–7.255 (m, 8 H).

IR (CDCl$_3$): 2971, 1629, 1589, 1490, 1417, 1217 cm$^{-1}$.

[1] U.S. Pat. No. 2,633,474 (CA 47:6171f). British Pat. No. 716,301 (CA 49:2112c). British Pat. No. 839,982 (CA 55:2166e).

5. Radioligand Binding Assays

PCP receptor binding assays were performed using guinea pig or rat brain membranes as the source of receptors. The radioligands used to label PCP receptors were (+)[$^3$H]MK-801 [97 Ci/mmol] and [$^3$H]TCP (55 Ci/mmol, New England Nuclear, Cambridge, MA).

Synthesis of (+)[$^3$H]MK-801 and PCP receptor binding assay protocols are described in Keana, J. F. W., Scherz, M.W. Quarum, M. Sonders, M. S. and Weber, E., Life Sci., in press (1988). Briefly, in the protocols, guinea pig brain membranes are prepared to a final protein concentration of 3 mg/ml and stored at −70° C. Rat brain membranes were prepared and used as described for "detergent-treated membranes" [see Murphy, D. E., Schneider, J., Boehm, C., Lehmann, J., and Williams, M., J. Pharmacol. Exp. Ther. 240, 778–784 (1987)], and stored at a protein concentration of 10 mg/ml at −70° C. No effect of storage (1 month) of the membranes at −70° C. on receptor number or affinity for (+)[$^3$H]MK-801 or [$^3$H]1-[1-(2-thienyl)cyclohexyl]-piperidine ([3H]TCP) was observed.

For radioreceptor binding assays with guinea pig membranes, aliquots were thawed and diluted with 5 mM Tris-HCl or Tris-acetate buffer (pH=7.4) to the concentration desired. The assays consist of 0.8 ml of membranes, 0.1 ml of radioactive tracer and 0.1 ml of buffer or unlabelled drug. For assays with rat membranes, the thawed membranes were incubated at 1 mg/ml with 0.01% Triton X-100 for 15 minutes at 32° C., then washed three times by centrifugation to reduce the endogenous amino acid concentrations, and finally resuspended in buffer for assay. Glycine and 1-glutamate were each added back to a final concentration of 1 uM to maximally stimulate the (+)[$^3$H]MK-801 or [$^3$H]TCP binding. The assays contain 400 ul of membranes, 50 ul of radioligand, and 50 ul of buffer or unlabelled drug.

For (+)[$^3$H]MK-801 binding, 1 nM radioligand was incubated with 120 ug/ml guinea pig brain membrane protein or 200 ug/ml of rat brain membranes for 4 hours at room temperature; for [$^3$H]TCP binding, 2 nM radioligand was incubated with 800 ug/ml of guinea pig brain membranes or 300 ug/ml of rat brain membranes for 45 minutes at room temperature. All assays were stopped by rapid filtration under vacuum through Whatman GF/B glass fiber filters using a Brandel 48-well cell harvester (Brandel, Gaithersburg, MD). The filters were presoaked in 0.05% polyethyleneimine when [$^3$H]TCP was used. The filters were washed three times with 5 ml of cold 5 mM tris-HCl, pH=7.4. Each filter was dissolved in 10 ml of Cytoscint (ICN Biomedicals, Costa Mesa, CA) and radioactivity was measured by liquid scintillation spectrometry at a counting efficiency of 50%.

Nonspecific binding was defined as that remaining in the presence of 10 uM TCP or (+)MK-801 for (+)[$^3$H]MK-801 binding and 100 uM PCP for [$^3$H]TCP binding. [$^3$H]CPP (3-((±)2-carboxy-piperazine-4-yl)-propyl-1-phosphonic acid) binding to the N-methyl-D-aspartate-type glutamate receptor [Murphy, D. E., Schneider, J., Boehm, C., Lehmann, J., and Williams, M., J. Pharmacol. Exp. Ther. 240, 778–784 (1987)], high affinity [$^3$H]kainate binding to the kainate-type glutamate receptor [Honore, T., Drejer, J., and Nielsen, M., Neuroscience Lett. 65, 47–52 (1986)], and [$^3$H]AMPA (DL-α-amino-3-hydroxy-5-methylisoxazole-4-propionic acid) binding to the quisqualate-type glutamate receptor [Murphy, D. E., Snowhill, E. W., and Williams, M., *Neurochem. Res.* 12, 775-782 (1987)] were assayed using rat brain membranes prepared as described above.

Saturation data were evaluated by Scatchard analysis using both the EBDA [McPherson, G. A., *Comput. Progcrams Biomed.* 77, 107-114 (1983)]and LIGAND [Munson, P. J. and Rodbard, D., *Anal. Biochem.* 107, 220-239 (1980)] data analysis programs. $IC_{50}$ values were determined by plotting displacement curves on semilogarithmic graph paper followed by interpolation.

DMTG, DOIPG, DMEPG, DOEPG and DTG were tested for binding to PCP receptor on guinea pig and rat brain membranes in radioligand binding assays using selective [$^3$H]-labelled ligands. (+)[$^3$H]MK-801 and [$^3$H]TCP were used to label PCP receptors. As can be seen in Tables I and II, DMTG, DOIPG, DOEPG and DMEPG had submicromolar affinities for PCP receptors as judged by their ability to displace the two selective PCP receptor ligands from binding to brain membranes from guinea pig (Table I) and rat (Table II). (The numbers in parentheses in Tables I and II indicate the number of experiments.) The parent compound DTG, by comparison, exhibited a low affinity for PCP receptors. Thus, the PCP receptors tolerate a wide range of structural alterations on compounds demonstrated to bind to these sites.

In contrast, none of the compounds tested showed significant binding affinity towards the N-methyl-D-aspartate-, kainate- or quisqualate-type glutamate binding sites, assayed using [$^3$H]CPP, [$^3$H]kainate and $^3$H]AMPA, respectively, as specific radioligands. DMTG and DOIPG did not cause more than 50% inhibition in these binding assays even at 100 uM, indicating that their neuroprotective actions were not due to the direct blocking of glutamate binding sites.

TABLE I

| | $IC_{50}$ [±SEM (n)] (nM) In Guinea Pig Brain Membranes vs. | | | |
|---|---|---|---|---|
| | $^3$H-MK801 | | $^3$H TCP | |
| DOIPG | 200 ± 40 | (3) | 260 ± 40 | (3) |
| DMTG | 280 ± 40 | (3) | 465 ± 30 | (3) |
| DMEPG | 189 ± 46 | (4) | 263 ± 70 | (4) |
| DOEPG | 540 ± 76 | (4) | 455 ± 87 | (4) |
| DTG | 6,800 ± 860 | (3) | 6,100 ± 700 | (3) |
| MK-801 | 3.9 ± 0.3 | (3) | 9.6 ± 1.6 | (5) |

TABLE II

| | $IC_{50}$ [±SEM (n)] (nM) In Rat Brain Membranes vs. | | | |
|---|---|---|---|---|
| | $^3$H-MK-801 | | 3H-TCP | |
| DOIPG | 240 ± 60 | (4) | 210 ± 60 | (4) |
| DMTG | 330 ± 30 | (4) | 370 ± 30 | (4) |
| DMEPG | 168 ± 38 | (6) | 82 ± 10 | (4) |
| DOEPG | 745 ± 90 | (4) | 358 ± 53 | (7) |
| DTG | 10,700 ± 2,100 | (3) | 7,800 ± 400 | (4) |
| MK-801 | 2.5 ± 0.6 | (4) | 3.2 ± 1.3 | (4) |

6. Electrophysiological Assays

The compounds were tested for their ability to achieve use-dependent blockage of NMDA-induced (+ glycine) responses on rat hippocampal neurons maintained in cell culture. DOIPG and DMTG were each tested. Each of these compounds produced results very similar to the use dependent blocking action exhibited by MK-801.

Hippocampal neurons were obtained from the CA1 region of the hippocampus from 1-3 day-old-newborn rats (Long-Evans). Small blocks of tissue ($<1$ mm$^3$) were incubated in papain (20 units ml$^{-1}$; Worthington-Cooper) for 30 minutes. The tissue was dissociated into a single cell suspension by trituration with a firepolished Pasteur pipette in complete growth medium (Earle's MEM, 20 mM glucose, 50 units/ml penicillin/streptomycin, 5% heat-inactivated fetal calf serum, Serum Extender from Collaborative Research) containing 2.5 mg/ml bovine serum albumin and 2.5 mg/ml trypsin inhibitor (Sigma). The cells were plated onto glass coverslips coated with collagen/poly-D-lysine. Cultures were fed every 3 days by replacing half the volume of medium. Arabinosylcytosine ($5 \times 10^{-6}$M) was added to the cultures for 1 or 2 days during the first week after plating to suppress the proliferation of non-neuronal cells.

All electrophysiology experiments were performed with the whole-cell or outside-out mode of patch clamp recording [Hamill, O. D., Marty, A., Neher, E., Sakman, B., and Sigworth, F. J., Pfluoers Arch. 391, 85-100 (1981)] from neurons grown for 1-3 weeks in culture. Agonists and antagonists were applied by pressure pipettes (Picospritzer; General Valve) to neurons in whole-cell experiments. Perfusion pipettes were used to apply drugs to outside-out patches by inserting the tip of the patch pipette into the opening of the perfusion pipette from which the test solution was flowing continuously. The external solution contained (in mM) NaCl 165, KCl 5, CaCl$_2$2, HEPES 5 (N-2-hydroxyethyl- piperazine-N'-2-ethanesulfonic acid pH adjusted to 7.4 with NaOH) and glycine 0.001 unless otherwise noted. The internal solution contained (mM) CsCl 160, EGTA 10 (ethyleneglycol-bis-($\beta$-aminoethylether)-N,N,N',N'-tetraacetic acid), HEPES 5 (pH adjusted to 7.4 with CsOH). Membrane current was filtered at 2000 Hz (single channel recording) or 200 Hz (whole-cell experiments) ($-3$ dB; 8-pole Bessel) and digitally sampled at 100 us or 8 ms intervals, respectively. Experiments were performed at room temperature (20°-25° C.). [Sources of chemicals: N-methyl-D-aspartate, Cambridge Research Biochemicals; salts for recording solutions, Aldrich (Gold Label) or Alfa (Puratronic). [$^3$H]Kainate and [$^3$H]CPP and [$^3$H]AMPA were purchased from Dupont/NEN (Boston, MA)].

One second applications of 50 uM NMDA in the presence of 1 uM glycine resulted in inward whole-cell currents of 100-400 pA at a holding potential of $-40$ mV. repetitive applications (every 30 s) to the same cell produced currents which varied less than 5% over a period of at least 30 minutes. When MK-801 (0.5-10 uM) was applied from the same pressure pipette as NMDA, the inward current became progressively smaller with serial applications. Recovery from this inhibition required repeated applications of NMDA alone and was speeded by holding the membrane potential at positive voltages. PCP (40 uM) produced similar effects. The effects of both antagonists were voltage-dependent; negative holding potentials augmented the blockade while at very positive potentials (+80 mV) little antagonism was observed.

Identical to MK-801, both DOIPG (3 and 30 uM) and DMTG (30 uM) inhibited the NMDA current in a usedependent and voltage-dependent manner. Serial applications evoked progressively smaller currents.

Inhibition by both DOIPG and DMTG was reversed only with prolonged or repeated application of NMDA. This reversal was increased by holding the membrane at positive potentials.

Single channel currents evoked by the appliction of NMDA to outside-out patches derived from the membrane of cultured rat hippocampal neurons were inhibited by DOIPG in a similar manner to their inhibition by MK-801. Prolonged exposure of the patch to these compounds in the presence of NMDA resulted in the diminution in the probability of channel opening as well as the mean channel open time. In the absence of antagonists, NMDA-evoked channel openings occurred with the same probability for at least 20 minutes. As with whole-cell recordings, the decreased probability of channel opening and mean open time were reversed by the prolonged presence of agonist without antagonist and recovery was enhanced by holding the membrane at positive potentials.

7. In Vitro Neurotoxicity Assay

Dissociated rat hippocampal cultures were prepared using a modification of the method of Huettner and Baughman [Huettner, J. E. and Baugham, R. W., *J. Neurosci.* 6 3044–3060 (1986)]. The cortices were removed from 1-3 day post-natal rats (Sprague-Dawley) that had been anesthetized with chloral hydrate, and the hippocampi were dissected out and placed in $Cl^-$ free dissociation
medium supplemented with 1 mM kynurenic acid and 10 mM $MgSO_3$ (Choi, D. W., *J. Neurosci.* 7, 369–379 (1987)). The hippocampi were washed in the dissociation medium, then incubated for $2 \times 20$ minutes at 37° C. in dissociation medium containing 10 units/ml of Papain (Worthington). After the enzyme treatment, the tissue was incubated for three 5-minute periods at 37° C. with 10 mg/ml trypsin inhibitor (Sigma type II-0).

The cells were dissociated by trituration in growth medium and plated as 0.15 ml droplets of cell suspension onto the center of 35 mm Primaria (Falcon) dishes that had been stamped with a labeled $26 \times 26$ grid of approximately 0.64 $cm^2$ total area using a Mecanex BB form (WPI, New Haven, Conn.) and coated with poly-D-lysine and laminin (Collaborative Research). The cell density was between 2.5 and $4.0 \times 10^5$ cells per dish. The growth medium was Eagles minimum essential media (MEM, Earle's salts) supplemented with 5% fetal bovine serum (CCL), 5% defined supplemented calf serum (HyClone), 50 mM glucose, 50 units/ml penicillin/streptomycin and MITO+serum extender (Collaborative Research). The cells were maintained at 37° C. in a humidified 4.5% $CO_2$ atmosphere. Cells were left for 12-14 hours to attach to the plate surface, then 1.5 mls of growth medium was added to each dish, 1 ml removed and replaced with a further 1 ml of fresh medium. This process removed most of the cell debris and unattached cells. The area of cell attachment and proliferation did not significantly extend beyond the treated central area. After 2-4 days in culture, non-neuronal cell division was arrested by a 2-3 day exposure to 5 uM cytosine arabinoside.

The cells were maintained in a medium that was similar to the growth medium but without the fetal bovine serum. The medium was changed on a weekly schedule, replacing two-thirds the volume with fresh medium. The only glutamate present in the media was that contained in the calf serum which gave a final concentration of 12 uM.

Before treatment, sister cultures were examined under phase-contrast microscopy to ensure that the cultures were of a similar density. Exposure to glutamate was carried out at 32°-34° C. in a HEPES-buffered "control salt solution" (CSS) similar to that reported in Choi, D. W., Maulicci-Gedde, M. and Viriegstein, A. R., *J. Neurosci.* 7, 257–268 (1987), but with 10 mM HEPES substituted for Tris-HCl and buffered for pH 7.4 at 34° C. The cultures were washed twice with CSS and then incubated for 5 minutes in CSS containing 1 uM glycine and the compound to be tested (the controls had 1 uM glycine only). Glycine was included since it has been shown to potentiate the effects of glutamate at the NMDA site [Johnson, J. W. and Ascher, P., *Nature* 325, 529–530 (1987)] and the preincubation with the test drugs enhances the neuroprotection activity (Finkbeiner, S. C., et al., *Proc. Natl. Acad. Sci. USA* 85:4071–4074 (1988)). CSS containing 1 uM glycine plus drug and a known concentration of glutamate (0–1000 uM) was added by triple exchange and the cultures incubated for 5 minutes. The cultures were washed four times with CSS and then with medium before being placed in the incubator overnight. Cultures were removed from the incubator the next day, washed twice with CSS and treated for 5 minutes with 0.4% Trypan Blue, a dye that is only taken up by dead and dying cells. The cultures were washed three times and the surviving cells counted in the grid area using phase contrast microscopy. Cell survival was normalized as a percentage of the highest cell count, and the results plotted against glutamate concentration. Cultures not exposed to glutamate generally had between 4500 and 5500 surviving cells in the grid area.

DOIPG, DMTG, DMEPG, DOEPG, their parent compound DTG, and MK-801 were tested for their neuroprotective properties against a range of glutamate concentrations. As illustrated in FIG. 1, cultures tested with 30 uM DOIPG, DMEPG, DOEPG or DMTG, or 0.5 uM MK-801 exhibited enhanced cell survival at glutamate concentrations of 30–1000 uM when compared to control values. The degree of neuroprotection afforded by these compounds, at the doses tested, was significant at $P < 0.05$ for glutamate concentration of 30 uM or greater (ANOVA and two-tailed t-test). By contrast, DTG failed to produce any significant neuroprotective response using a dose of 30 uM.

8. In Vivo Neurotoxicity Assay

The experimental model of McDonald, J. W., et al., supra, was employed with the single alteration in protocol of an intraperitoneal injection of the test compound 15 minutes following, rather than preceding, the cerebral NMDA injection. DOIPG, DMTG and DMEPG were tested in this assay and were found, in dosages ranging from about 10 to 100 uM/kg of body weight to protect against the lesions caused by NMDA injection.

These observations on the in vitro and in vivo neuroprotective properties of DOIPG, DMTG, DMEPG, and DOEPG are consistent with their affinity for the PCP binding site in brain and the inhibition of the NMDA current described above.

The di-substituted guanidines of the present invention are chemically unrelated to any known NMDA channel blockers acting through PCP receptors. As discussed above, previously, only compounds belonging to the PCP/ketamine series, benzomorphan opiates, benz-f-isoquinolines and MK-801 were known to interact with PCP receptors [see Zukin, R. S. and Zukin, S. R.,

*Trends in Neurosci.,* in press (1988); Sonders, M. S., Keana, J. F. W. and Weber, E., *Trends in Neurosci.* 11(1), 37-40 (1988); Wong, E. H. F., Kemp., J. A., Priestly, T., Knight, A. R., Woodruff, G. N. and Iversin, L. I., *Proc. Natl. Acad. USA* 83, 7104-7108 (1986)].

The compounds of this invention could be administered intranasally, orally or by injection, e.g., intramuscular, intraperitoneal or intravenous. The optimal dose can be determined by conventional means. Because most if not all of the N,N'-disubstituted guanidines employed in this invention are substantially water insoluble, they are ordinarily administered in the protonated form, e.g., as a pharmaceutically acceptable salt of an organic or inorganic acid, e.g., hydrochloride, sulfate, hemi-sulfate, phosphate, nitrate, acetate, oxalate, citrate, etc.

The compounds of this invention can be employed in mixture with conventional excipients, i.e., pharmaceutically acceptable organic or inorganic carrier substances suitable for parenteral, enteral or intranasal application which do not deleteriously react to the active compounds. Suitable pharmaceutically acceptable carriers include but are not limited to water, salt solutions, alcohol, vegetable oils, polyethylene glycols, gelatin, lactose, analose, magnesium stearate, talc, silicic acid, biscus paraffin, perfume oil, fatty acid monoglycerides and diglycerides, petroethral fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or a carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Parenteral administration, e.g., IP or IM, is preferred, the compounds of this invention being particularly valuable in the treatment of mammalian subjects, e.g., humans, wherein the pathophysiology of the disease involves excessive excitation of nerve cells by agonists of the NMDA receptor. Typically, such subjects include those afflicted with neurodegenerative diseases such as Huntington's chorea, Amyotrophic Lateral Sclerosis, Alzheimer's disease, and Down's Syndrome. Also suitable for treatment are those subjects suffering from nervous system dysfunctions resulting from, for example, epilepsy, and nerve cell degeneration which is the result of hypoxia, ischemia, hypoglycemia, or trauma. Typical candidates for treatment include heart attack, stroke, brain, and spinal cord injury patients.

It will be appreciated that the actually preferred amounts of active compounds used will vary according to the specific compound being utilized, the particular compositions formulated, the mode of application and the particular site of administration. Optimal administration rates for a given protocol of administration can be readily ascertained by those skilled in the art using conventional dosage determination tests conducted with regard to the foregoing guidelines.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A neuroprotecting N,N'-disubstituted guanidine which exhibits a high binding activity with respect to the PCP receptor in mammalian nerve cells selected from the group consisting of N,N'-di-o-iodo-phenyl-guanidine; N,N'-di-m-tolyl-guanidine; N,N'-di-o-ethylphenyl guanidine; N,N'-di-m-ethylphenyl guanidine; and physiologically acceptable salts thereof.

2. N,N-di-o-ethylphenyl guanidine, a compound of claim 1.

3. N,N'-di-m-ethylphenyl guanidine, a compound of claim 1.

4. N,N-di-m-tolyl guanidine, a compound of claim 1.

5. N,N'-di-o-iodo-phenyl-guanidine, a compound of claim 1.

6. A method for treating a disease of the nervous system in which the pathophysiology of the disorder involves excessive excitation of nerve cells by agonists of NMDA receptors comprising the administration to a mammal exhibiting symptoms of such disorders or susceptible to such disorders, a N,N'-disubstituted guanidine having a high affinity for the PCP receptor of the nerve cell in an amount effective to block the ion channel of the NMDA-receptor ion-channel complex.

7. A method according to claim 6, said N,N'-disubstituted guanidine having the formula

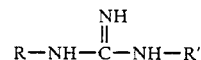

wherein R and R, each are an alkyl group of 4-12 carbon atoms, a cycloalkyl group of 3-12 carbon atoms, carbocyclic aryl, alkaryl, or aralkyl of 6-18 carbon atoms and containing 1-3 separate or fused rings, or a heterocyclic compound, and further wherein each of R and R' may be substituted in 1-3 positions.

8. A method according to claim 7, wherein the N,N'-disubstituted guanidine is selected from the group consisting of N,N'-di-m-tolyl-guanidine; N,N'-di-o-iodophenyl-guanidine; N,N'-di-o-ethylphenyl-guanidine; and N,N'-di-m-ethylphenyl-guanidine and physiologically acceptable salts thereof.

9. A method according to claim 7, wherein said N,N'-disubstituted guanidine is N,N'-di-m-tolylguanidine.

10. A method according to claim 7, wherein said N,N'-disubstituted guanidine is N,N'-di-o-iodo-phenyl-guanidine.

11. A method according to claim 7, wherein said N,N'-disubstituted guanidine is N,N'-di-o-ethylphenyl guanidine.

12. A method according to claim 7, Wherein said N,N'-disubstituted guanidine is N,N'-di-m-ethylphenyl guanidine.

13. A method according to claim 6, wherein said neurotoxicity is associated with Alzheimer's disease, Huntington's chorea, Amyotrophic Lateral Sclerosis, or Down's Syndrome.

14. A method according to claim 13, wherein N,N' disubstituted guanidine is selected from the group consisting of N,N'-di-m-tolyl-guanidine; N,N'-di-o-iodophenyl-guanidine; N,N'-di-o-ethylphenyl-guanidine; and N,N'-di-m-ethylphenyl-guanidine and physiologically acceptable salts thereof.

15. A method according to claim 14, wherein the N,N'-disubstituted guanidine is N,N'-di-m-tolylguanidine.

16. A method according to claim 14, wherein the N,N'-disubstituted guanidine is N,N'-di-o-iodo-phenyl-guanidine.

17. A method according to claim 14, wherein said N,N'-disubstituted guanidine is N,N'-di-o-ethylphenyl guanidine.

18. A method according to claim 14, wherein said N,N'-disubstituted guanidine is N,N'-di-m-ethylphenyl guanidine.

19. A method according to claim 6, wherein the mammal is a human being suffering from epilepsy or memory disorder.

20. A method according to claim 19, Wherein the N,N'-disubstituted guanidine is selected from the group consisting of N,N'-di-m-tolyl-guanidine; N,N'-di-o-iodophenyl-guanidine; N,N'-di-o-ethylphenyl-guanidine; and N,N'-di-m-ethylphenyl-guanidine and physiologically acceptable salts thereof.

21. A method according to claim 19, wherein the N,N'-disubstituted guanidine is N,N'-di-m-tolylguanidine.

22. A method according to claim 19, wherein the N,N'-disubstituted guanidine is N,N'-di-o-iodo-phenyl-guanidine.

23. The method according to claim 19, wherein the N,N'-disubstituted guanidine is N,N'-di-o-ethylphenyl guanidine.

24. The method according to claim 19, wherein the N,N'-disubstituted guanidine is N,N'-di-m-ethylphenyl guanidine.

25. A method of inhibiting NMDA receptor-ion channel related neurotoxicity comprising administering to a mammal a N,N'-disubstituted guanidine possessing a high affinity for the PCP receptor of a nerve cell, in an amount effective to inhibit the neurotoxicity.

26. A method according to claim 25, wherein said neurotoxicity is caused by excessive release of endogenous glutamate following the occurrence of ischemic brain insults.

27. A method according to claim 25, wherein the N,N'-disubstituted guanidine is selected from the group consisting of N,N'-di-m-tolyl-guanidine; N,N'-di-o-iodophenyl-guanidine; N,N'-di-o-ethylphenyl-guanidine; and N,N'-di-m-ethylphenyl-guanidine and physiologically acceptable salts thereof.

28. A method according to claim 25, wherein the N,N'-disubstituted guanidine is N,N'-di-m-tolylguanidine.

29. A method according to claim 25, wherein the N,N'-disubstituted guanidine is N,N'-di-o-iodo-phenyl-guanidine.

30. The method according to claim 25, wherein the N,N'-disubstituted guanidine is N,N'-di-o-ethylphenyl guanidine.

31. The method according to claim 25, wherein the N,N'-disubstituted guanidine is N,N'-di-m-ethylphenyl guanidine.

32. A method according to claim 6, wherein said N,N'-disubstituted guanidine is administered at a dosage of about 10–100 um/kg of body weight.

33. A method according to claim 25, wherein said N,N'-disubstituted guanidine is administered at a dosage of about 10–100 um/kg of body weight.

* * * * *

UNITED STATES PATENT AND TRADEMARK OFFICE
CERTIFICATE OF CORRECTION

PATENT NO. : 4,906,779
DATED : March 6, 1990
INVENTOR(S) : ECKARD WEBER ET AL

It is certified that error appears in the above-identified patent and that said Letters Patent is hereby corrected as shown below:

Column 16, claim 2, line 23:

reads "N,N-di-o-ethylphenyl guanidine, a compound of"

should read -- N,N'-di-o-ethylphenyl guanidine, a compound of --

Column 16, claim 4, line 27:

reads "N,N-di-m-tolyl guanidine, a compound of claim 1.

should read -- N,N'-di-m-tolyl guanidine, a compound of claim 1. --

Column 16, claim 7, line 46:

reads "wherein R and R, each are an alkyl group of 4-12 car-"

should read -- wherein R and R', each are an alkyl group of 4-12 car- --

Signed and Sealed this

Eighteenth Day of June, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,906,779

DATED : March 6, 1990

INVENTOR(S) : Weber et al.

It is certified that error appears in the above-identified patent and that said Letters Patent is hereby corrected as shown below:

Column 1, line 3, before "BACKGROUND OF THE INVENTION" please insert the following text:

-- This invention was made with government support under Grant No. MH 40303 awarded by the National Institutes of Health. The government has certain rights in the invention.--

Signed and Sealed this

Second Day of March, 1993

*Attest:*

STEPHEN G. KUNIN

*Attesting Officer*   *Acting Commissioner of Patents and Trademarks*